US006417419B1

(12) United States Patent
Abrevaya et al.

(10) Patent No.: US 6,417,419 B1
(45) Date of Patent: Jul. 9, 2002

(54) PROCESS FOR HYDROGENATING ACETYLENES

(75) Inventors: Hayim Abrevaya, Wilmette; Deng Yang Jan, Elk Grove Village; Karl Z. Steigleder, Glen Ellyn, all of IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 09/784,260

(22) Filed: Feb. 16, 2001

(51) Int. Cl.$^7$ .......................... C07C 7/167; C07C 7/163
(52) U.S. Cl. ...................... 585/260; 585/258; 585/259
(58) Field of Search ............................. 585/258, 259, 585/260

(56) References Cited

U.S. PATENT DOCUMENTS

| | | | |
|---|---|---|---|
| 3,218,268 A | 11/1965 | Arnold | 252/465 |
| 3,259,454 A | 7/1966 | Michalko | 23/2 |
| 3,259,589 A | 7/1966 | Michalko | 252/466 |
| 3,388,077 A | 6/1968 | Hoekstra | 252/466 |
| 3,751,508 A | 8/1973 | Fujiso et al. | 260/677 |
| 3,912,789 A | 10/1975 | Frevel et al. | 260/681.5 |
| 4,493,906 A | 1/1985 | Couvillion | 585/260 |
| 4,903,906 A | 1/1985 | Couvillion | 502/346 |

OTHER PUBLICATIONS

Sarkany, A.; Weiss, A. H.; Szilagyi, T.; Sandor P.; Guczi L. *Applied Catalysis* 1984, 12, 373–379.
Lee, S.; Aris, R. *Catal. Rev.–Sci. Eng.* 1985, 27(2), 207–340.
Komiyama, M. *Catal. Rev.–Sci. Eng.* 1985, 27(2), 341–372.
Dougherty, R. C.; Verykios, X. E. *Catal. Rev.–Sci. Eng.* 1987, 29(1), 101–150.

Primary Examiner—Thuan D. Dang
(74) Attorney, Agent, or Firm—John G. Tolomei; Frank S. Molinaro; Maryann Maas

(57) ABSTRACT

A process for selectively hydrogenating C4-acetylenes in a liquid hydrocarbon stream containing largely butadiene has been developed. Hydrogen and the hydrocarbon stream are contacted with a catalytic composite comprising an inorganic oxide support having dispersed thereon finely divided copper metal and an activator metal of nickel, cobalt, platinum, palladium, manganese, or a combination thereof where 1) the catalytic composite has an average diameter of up to about 1/32 inch (800 microns) and/or 2) at least 70 weight percent of the copper metal and the activator metal are dispersed on the outer 200 micron layer of the support.

8 Claims, 6 Drawing Sheets

US 6,417,419 B1

PROCESS FOR HYDROGENATING ACETYLENES

FIELD OF THE INVENTION

A process for the selective hydrogenation of $C_4$-acetylenes in the presence of butadiene with the added benefit of extended catalyst stability has been developed.

BACKGROUND OF THE INVENTION

Butadiene is an important starting material for the production of high molecular weight polymers and is used extensively to form synthetic rubber including styrene-butadiene rubber, nitrile-butadiene rubber, buna-S rubber, and trans-polybutadiene rubber, and adiponitrile and styrene butadiene latex in paints. Butadiene is usually a by-product from steam cracking naphtha. However, the product butadiene regularly contains impurities that must be removed before the butadiene may be used as a starting material. The principal impurities are acetylenes including ethylacetylene, methylacetylene and vinylacetylene. Historically, two approaches have been used to remove the acetylenes: extractive distillation using a solvent to selectively absorb the acetylenes, or selective hydrogenation of the acetylenes.

In using selective hydrogenation, copper-containing catalytic composites have been shown to be successful. Copper-containing catalytic composites used for selective hydrogenation of acetylenes are disclosed in U.S. Pat. No. 4,493,906 which discloses the catalyst as 1/16 inch extrudates, U.S. Pat. No. 4,440,956 which discloses the catalysts as 1/8 inch pellets, U.S. Pat. No. 3,912,789, U.S. Pat. No. 3,218,268 which disclose the catalysts as 3/16 inch tablets, and U.S. Pat. No. 3,751,508 which disclose the catalysts as 3 mm tablets (about 1/8 inch tablet). In contrast to this art, applicants have discovered that a copper-containing catalytic composite where. at least 70 weight percent of the copper and optionally one or more activator metals are dispersed on the outer 200 microns of the catalyst support. It is most preferred that the catalyst composite particles also have an average diameter of about 1/32 inch (800 microns) or less. A microsphere catalyst is shown herein to have much improved stability and selectivity versus similar catalysts having particles of about 1/16 inch (1600 microns) diameter.

SUMMARY OF THE INVENTION

The present invention is related to a process for selectively hydrogenating $C_4$-acetylenes in a liquid hydrocarbon stream containing largely butadiene with the benefit of increased catalyst stability. Hydrogen and the hydrocarbon stream are contacted with a catalytic composite comprising an inorganic oxide support having dispersed thereon finely divided copper metal and optionally an activator metal selected from the group consisting of nickel, cobalt, platinum, palladium, manganese, and a combination thereof where at least 70 weight percent of the copper metal and the activator metal are dispersed on the outer 200 micron layer of the support. In a specific embodiment of the invention, at least 80 weight percent of the copper metal is dispersed on the outer 200 micron layer of the support. In another specific embodiment of the invention, hydrogen and the hydrocarbon stream are contacted with a catalytic composite comprising an inorganic oxide support having dispersed thereon finely divided copper metal and optionally an activator metal selected from the group consisting of nickel, cobalt, platinum, palladium, manganese wherein the catalytic composite is spherical and has an average diameter of about 1/32 inch (800 microns) or less.

BRIEF DESCRIPTION OF THE DRAWINGS

The figures contain the results of the accelerated stability experiments conducted in Example 3.

DETAILED DESCRIPTION OF THE INVENTION

Figure 1:
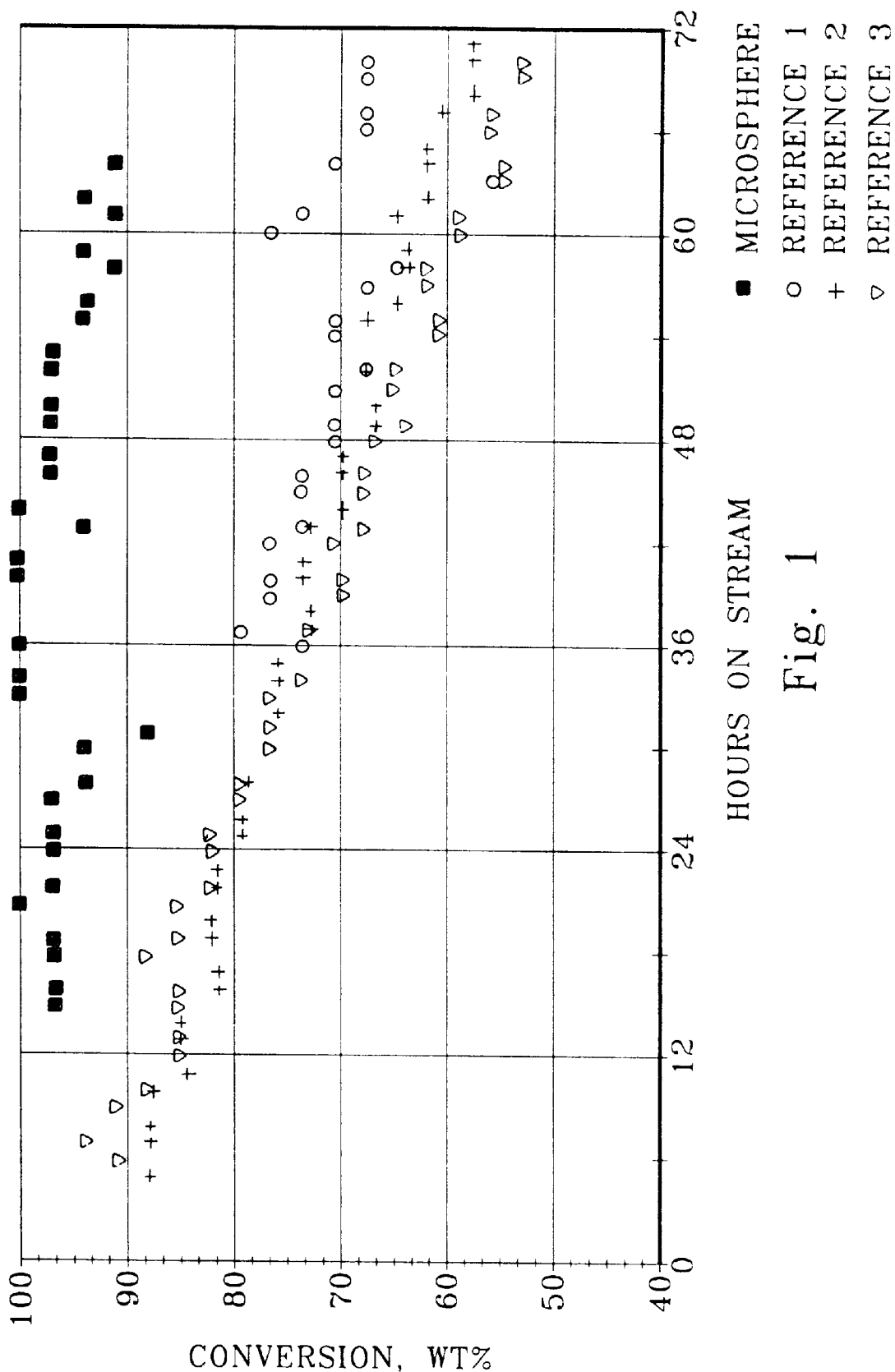
FIG. 1 shows the weight percent conversion of vinyl acetylene over time when using a microspherical catalyst of the present invention as compared to three reference catalysts.

In general terms, the invention is a process for selectively hydrogenating $C_4$-acetylenes in the presence of large amounts of butadiene by contacting the hydrocarbons with a supported catalytic composite where at least 50 weight percent of the active catalytic agents, preferably at least 70 weight percent, more preferably at least 80 weight percent, and most preferably at least 88 weight percent, are located on the outer 200 micron layer of the support. Another embodiment of the invention is one where the support is spherical and has an average diameter of less than about 1/32 inch (800 microns). The invention further reduces the production of undesired high molecular weight polymerized byproducts thereby extending the stability and enhancing the selectivity of the catalyst. The term "$C_4$-acetylenes" as used herein is meant to include vinylacetylene, ethylacetylene, and methylacetylene. The vinylacetylene is hydrogenated to 1,3-butadiene, the ethylacetylene is hydrogenated to 1-butene, and the methylacetylene is hydrogenated to propylene.

The $C_4$-acetylenes are typically formed as a byproduct in butadiene production and must be removed before the butadiene can be further processed. The acetylenes are may be in a concentration ranging from about 0.5 to about 3 weight percent, or higher, of the product liquid hydrocarbon stream from a butadiene production reactor. The liquid hydrocarbon stream generally contains butadiene (40–50 weight percent), butenes (40–50 weight percent), butanes (5–10 weight percent) and $C_4$-acetylenes. Propane and $C_3$-acetylenes are also present in minor quantities. In a typical treating process, hydrogen and the hydrocarbon stream are introduced to a fixed bed reactor. Various methods of introducing hydrogen to the reactor are known and any such method is suitable for use in this invention. The preferred method is to admix the hydrocarbon stream with a stoichiometric amount of hydrogen and then introducing the mixture to a fixed bed reactor.

The fixed bed reactor contains a catalytic composite effective to catalyze the selective hydrogenation of the acetylenes. The catalytic composite must be "selective" to the acetylenes so as to minimize hydrogenation of the desired butadiene. The catalytic composite contains finely divided copper metal and one or more activator metals which are bound to a support. The activator metals are those which are normally introduced in the form of salts and whose oxides are reducible by hydrogen. Suitable activator metals include nickel, cobalt, manganese, platinum, palladium, or a combination thereof. The most preferred activator metal is nickel. The copper is present in an amount ranging from about 5 to about 15 weight percent of the whole finished catalytic composite in the oxidized form and the activator metal is present in an amount ranging from about 0.1 to about 1 weight percent of the whole finished catalytic composite in the oxidized form. Suitable methods of depositing the metals on the support are discussed below.

The support may be refractory inorganic oxide materials such as silica, alumina, carbon, titania, magnesia, zirconia, clays, zeolites, and a combination thereof. The aluminas which can be used as a support include gamma, theta, delta, and alpha alumina with gamma and theta alumina being preferred. The zeolites which can be used include faujasites, zeolite Beta, L-zeolite, ZSM-5, ZSM-8, ZSM-11, ZSM-12, and ZSM-35. The preferred refractory inorganic oxides are gamma and theta alumina.

The support may be of any suitable size and shape including spherical and extruded supports. The extruded support is prepared as commonly known in the art.

The extrudate is preferably cylindrical with 1/32 inch diameter. The support may also be a shaped support such as a trilobe, quadrulobe, irregular shaped particles, pellets, or hollow tube which preferably posses a maximum diffusion path of 1/32 inch or less. The support may also be spherical with typical sphere sizes used in process such as these include 1/16 inch and 1/8 inch. A preferred spherical support is of a "microsphere" size, which includes spheres of support material nominally having a diameter of about 1/32 inch (800 microns) or less. The spheres are preferably produced by commonly known oil-dropping techniques such as described in U.S. Pat. No. 2,620,314, which is incorporated by reference. The oil drop method comprises forming an aluminum hydrosol by any of the techniques taught in the art and preferable by reacting aluminum metal with hydrochloric acid; combining the hydrosol with a suitable gelling agent, e.g., hexamethylenetetramine; and dropping the resultant mixture into and oil bath maintained at elevated temperatures, The droplets of the mixture remain in the oil bath until they set and form hydrogel spheres. The spheres are then continuously withdrawn from the oil bath and typically subjected to specific aging and drying treatments in oil and ammoniacal solutions to further improve their physical characteristics. The resulting aged gel spheres are then washed at about 70° C. to about 100°C. and dried at a relatively low temperature of about 65° C. to about 260° C. then calcined at a temperature of about 455° C. to about 705° C. for a period of about 1 to about 20 hours. This treatment effects conversion of the hydrogel to the corresponding crystalline gamma-alumina. If theta alumina is desired then the hydrogel spheres are 20 calcined at a temperature of about 950° C. to about 1200° C.

While microspheres are preferred, a variety of support shapes are suitable, as discussed above. It is preferred that the support, whether spherical or not, have an effective diameter of about 1/32 inch (800 microns) or less. For a non-spherical support, effective diameter is defined as the diameter of the shaped article would have if it were molded into a sphere.

The catalytic metal copper, and the activator metal(s) may be dispersed onto the support by means well known in the art such as impregnation, coprecipitation, cogellation or ion exchange. The preferred method of incorporating the metal copper and the activator metals is impregnation of the support with a solution containing one or more decomposable compound of the desired metal(s) followed by calcination. Illustrative of the decomposable compounds which can be used are: copper nitrate, copper acetate, copper acetylacetonate, nickel nitrate, nickel carbonate, nickel acetate, nickel acetylacetonate, manganese nitrate, manganese acetate, manganese acetylacetonate, manganese carbonate, manganese carbonyl, cobalt nitrate, cobalt acetate, cobalt acetylacetonate, cobalt carbonate, chloroplatinic acid, platinum tetrachloride, palladic acid, palladium chloride, and palladium nitrate.

Various impregnation techniques can be used including dip, evaporative and vacuum impregnation. One preferred method of impregnation involves the use of a steam-jacketed rotary evaporator. The desired support is immersed in an impregnating solution containing the desired metal(s) in the drier and the support is tumbled therein by the rotary motion of the drier. Evaporation of the solution in contact with the tumbling support is expedited by applying the steam to the drier jacket. The resultant catalytic composite is dried and then calcined.

In one embodiment of the invention, a microspherical catalytic composite is used. The microspherical catalytic composite has several advantages over previously disclosed catalysts. It is well known that a portion of the acetylenes present in the hydrocarbon stream will tend to polymerize and form high molecular weight undesirable byproducts, see, Sarkany, A.; Weiss, A. H.; Szilagyi, T.; Sandor P.; Guczi L. *Applied Catalysis* 1984, 12, 373–379. Furthermore, much of the polymerization occurs within the pores of the catalytic composite with the polymerized products remaining trapped within the pores and decreasing the activity of the catalyst. As the activity of the catalyst declines, the selective nature of the hydrogenation lessens and the amount of hydrogenation of butadiene relative to the amount of hydrogenation of acetylenes is increased. Through using a microspherical catalytic composite, the residence time of the acetylene within the catalyst before being hydrogenated is reduced thereby decreasing the opportunity for the acetylene to polymerize. In other words, the diffusion path length of the acetylene through the composite is reduced allowing for more rapid hydrogenation and less acetylene is available for polymerization. Reducing the amount of acetylene polymerization results in increased catalytic composite stability and enhanced selectivity as demonstrated in the Examples. With increased stability, the catalyst may be operated at less severe conditions for a longer period of time with fewer periodic regeneration cycles and no loss of acetylene conversion. In addition, the product effluent is of higher purity and requires less intense downstream purification processing. Larger diameter catalysts are expected to provide the same advantages as discussed above when at least 50 and preferably 70 weight percent of the copper metal and the activator metals are dispersed on the outer 200 microns of the catalyst support.

In a preferred embodiment, the copper and the activator metals may be incorporated on the catalytic support using the aforementioned evaporative impregnation technique, where at least 50 weight percent of the metals are located in the outer 200 micron layer of the support, preferably where at least 70 weight percent of the metals are located in the outer 200 micron layer of the support, and more preferably where at least 80 weight percent of the metals are located in the outer 200 micron layer of the support. It is most preferred that at least 88 weight percent of the metals are located on the outer 200 micron layer of the support. "Layer" is meant to describe a stratum of substantially uniform thickness, and "outer" is meant to define the exterior layer of the support. In general terms, surface impregnation can be carried out using metal complexes that have a high affinity for the support surface or complexes which are bulky in nature. It can also be achieved by spray impregnation techniques in which the volume of the impregnating solution is less than that required to fill the pore volume. Techniques for surface impregnation are known in the art and are described in U.S. Pat. No. 3,259,454, U.S. Pat. No. 3,259,589, U.S. Pat. No. 3,388,077, Lee, S.; Aris, R. *Catal. Rev.-Sci. Eng.* 1985, 27(2), 207–340; Komiyama, M. *Catal. Rev.-Sci. Eng.* 1985, 27(2), 341–372; and Dougherty, R. C.; Verykios, X. E. *Catal. Rev.-Sci. Eng.* 1987, 29(1), 101–150.

Selective hydrogenation of the acetylenes is carried out by contacting the hydrocarbons with the above-described catalytic composite in a fixed bed system. The hydrocarbon may be preheated to the processing temperature and hydrogen is admixed. Alternatively, the hydrocarbon and hydrogen may be mixed before preheating the mixture to the process temperature. This reactant mixture is passed to the fixed bed system which may be a single bed, or multiple sub-beds with heating means situated between the individual beds to maintain the reactants at the desired temperature. The fixed bed system may also be operated in a swing bed mode, with one sub-bed on-line and receiving the reactant mixture while another sub-bed is off-line. The catalytic composite containing in the sub-bed off-line may be in the process of being regenerated, or may have completed regeneration and is ready for use. As the reactant mixture contacts the catalytic composite, the acetylenes are hydrogenated leaving the effluent stream essentially acetylene-free. Examples of the selective hydrogenation reactions include hydrogenating vinyl acetylene to form 1,3-butadiene, hydrogenating ethyl acetylene to form 1-butene, and hydrogenating methyl acetylene to form propylene. The amount of residual acetylenes expected in the reactor effluent is typically less than 15 wt-ppm. Conditions for the selective hydrogenation of $C_4$-acetylenes include a temperature in the range of about 20° C. to about 80° C., pressures in the range of from about 15 bars to about 50 bars and liquid hourly space velocities in the range of from about 0.5 to about 10. Hydrogen is also added at a hydrogen to acetylene ratio of from about 1.0 to about 5.0.

The following example is presented as an illustration of one specific embodiment of this invention and is not intended as undue limitations of the generally broad scope of the intention as set forth in the claims. The specific embodiment involves a process for selectively hydrogenating C4-acetylenes in a liquid hydrocarbon stream containing largely butadiene comprising contacting hydrogen and the hydrocarbon stream with a catalytic composite which is an inorganic oxide support having dispersed thereon finely divided copper metal and optionally an activator metal selected from the group consisting of nickel, cobalt, platinum, palladium, manganese, and a combination thereof where the catalytic composite is spherical and has an average diameter of up to about 1/32 inch (800 microns).

EXAMPLE 1

Alumina spheres were prepared by the well known oil drop method which involves forming an aluminum hydrosol by dissolving aluminum in hydrochloric acid. To this hydrosol, where was added hexamethylene tetraamine to gel the mixture into spheres when dispersed into droplets into an oil bath maintained at about 93° C. The droplets remained in the oil bath until they set and formed hydrogel spheres. After the spheres were removed from the hot oil, they were pressure aged at 130° C. and washed with dilute ammonium hydroxide solution, dried to 260° C. and calcined at 640° C. for about 1.5 hours to give gamma alumina spheres having an average diameter of 1/16 inch (1600 microns).

The metal incorporation was performed using the evaporative impregnation technique. First, the impregnation solution was prepared by dissolving copper nitrate, nickel nitrate, cobalt nitrate, and manganese nitrate in water. The resultant solution was then added to a rotary evaporator loaded with the gamma alumina spheres. After cold rolling the mixture for 1 hour steam was introduced to the outer jacket to evaporate the excess water. The metal impregnated catalyst was dried at 210° C. for 1 hour and calcined at 400° C. for 2 hours. The above process was repeated three times to give three reference catalysts having 1/16 inch diameter spheres, identified as Reference 1, Reference 2, and Reference 3.

EXAMPLE 2

Again, alumina spheres were prepared by the well known oil drop method. involving forming an aluminum hydrosol by dissolving aluminum in hydrochloric acid. To this hydrosol, where was added hexamethylene tetraamine to gel the mixture into spheres when dispersed into droplets into an oil bath maintained at about 93° C. The droplets remained in the oil bath until they set and formed hydrogel microspheres, After the microspheres were removed from the hot oil, they were pressure aged at 120° C. and washed with dilute ammonium hydroxide solution, dried at 205° C. and calcined at 640° C. for about 1.5 hours to give gamma alumina microspheres having an average diameter of 1/32 inch (800 microns).

The metal incorporation was performed using the evaporative impregnation technique. First, the impregnation solution was prepared by dissolving copper nitrate, nickel nitrate, cobalt nitrate, and manganese nitrate in water. The resultant solution was then added to a rotary evaporator loaded with the gamma alumina spheres. After cold rolling the mixture for 1 hour steam was introduced to the outer jacket to evaporate the excess water. The metal impregnated catalyst was dried at 210° C. for 1 hour and calcined at 400° C. for 2 hours.

The microspherical catalyst was analyzed and compared to the reference catalysts prepared in Example 1. Table 1 shows the results of the microspherical catalyst analysis as compared to the typical result for the three reference catalysts with all concentration units in weight percent of the catalytic composite.

TABLE 1

|  | 1/32 inch | 1/16 inch |
| --- | --- | --- |
| copper, wt. % | 7.1 | 7.6 |
| nickel, wt. % | 0.2 | 0.19 |
| cobalt, wt. % | 0.10 | 0.10 |
| manganese, wt. % | 0.15 | 0.14 |
| average bulk density in g/cc | 0.73 | 0.80 |
| BET surface area, m$^2$/g | 179 | 182 |

EXAMPLE 3

The catalysts prepared in Examples 1 and 2 were evaluated in a selective hydrogenation process with the results demonstrating the enhanced stability and selectivity of the microspherical catalyst of Example 2 as compared to Reference catalysts 1, 2, and 3 of Example 1. A reactor was loaded with 16 g of the microspherical catalyst prepared in Example 2 and heated to an inlet temperature of 60° C. A crude C$_4$ hydrocarbon stream from a naphtha cracker complex and containing about 38 wt. % 1,3-butadiene and 0.35 weight percent of vinyl. acetylene and 0.13 wt. % ethylacetylene was introduced to the reactor at an acetylene weight hourly space velocity of 0.15. The hydrogen to acetylene molar ratio was 2.1. The effluent was analyzed by gas chromatography and the resulting data is provided in FIGS. 1–6. The experiment was repeated three more times at the same conditions to test Reference catalysts 1, 2, and 3 of Example 1. To test Reference catalyst 1, the reactor was loaded with 16 g of Reference catalyst 1 prepared in Example 1. To test Reference catalyst 2, the reactor as loaded with 16 g of Reference catalyst 2 prepared in Example 1. To test Reference catalyst 3, the reactor was loaded with 16 g of Reference catalyst 3 prepared in Example 1. The results of all analyses are provided in FIGS. 1–6.

Figure 2:
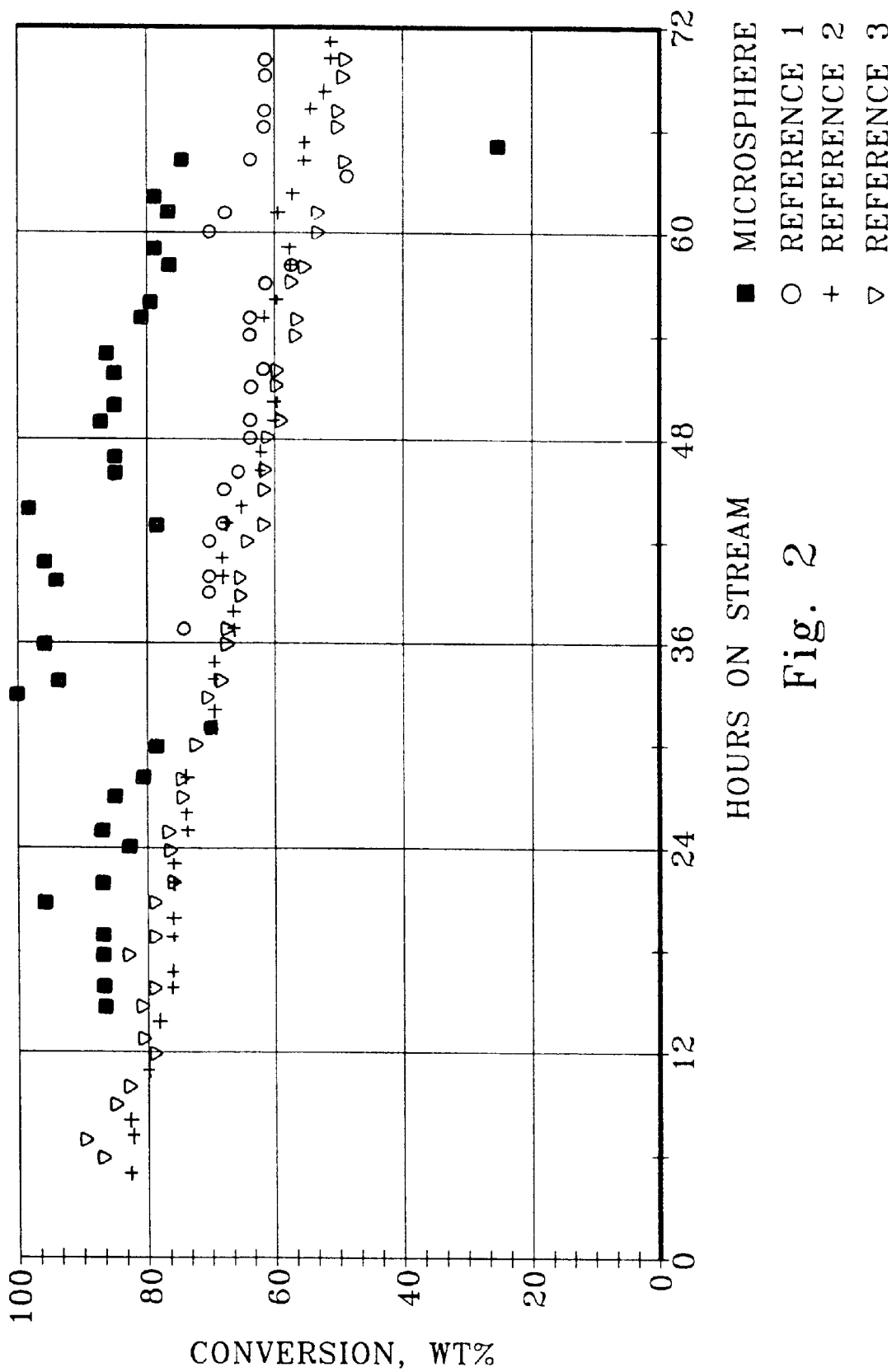
FIG. 2 shows the weight percent conversion of total acetylenes over time when using a catalyst of the present invention as compared to three reference catalysts.
Figure 3:
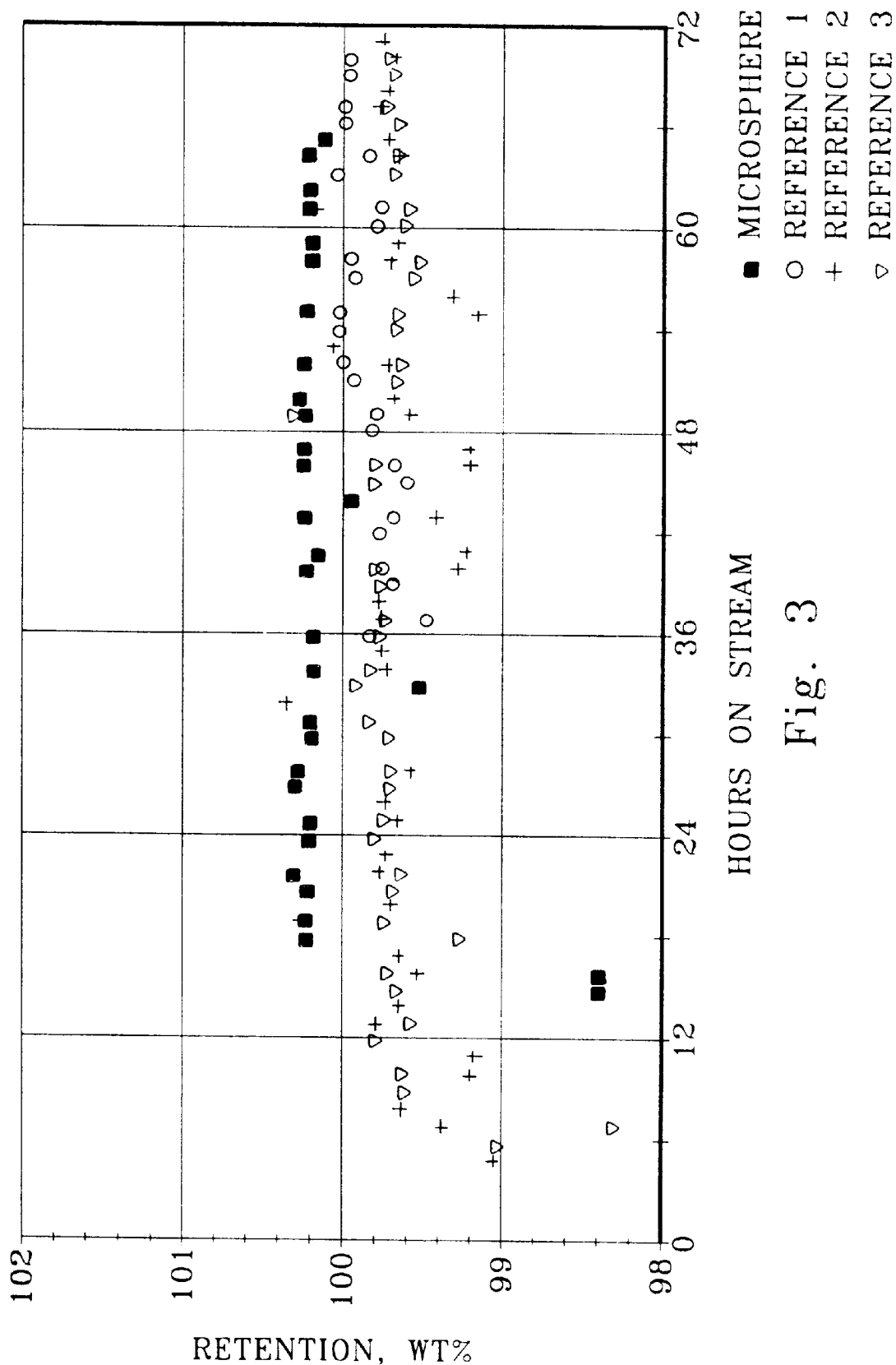
FIG. 3 shows 1,3-butadiene retention over time when using a catalyst of the present invention as compared to three reference catalysts.
Figure 4:
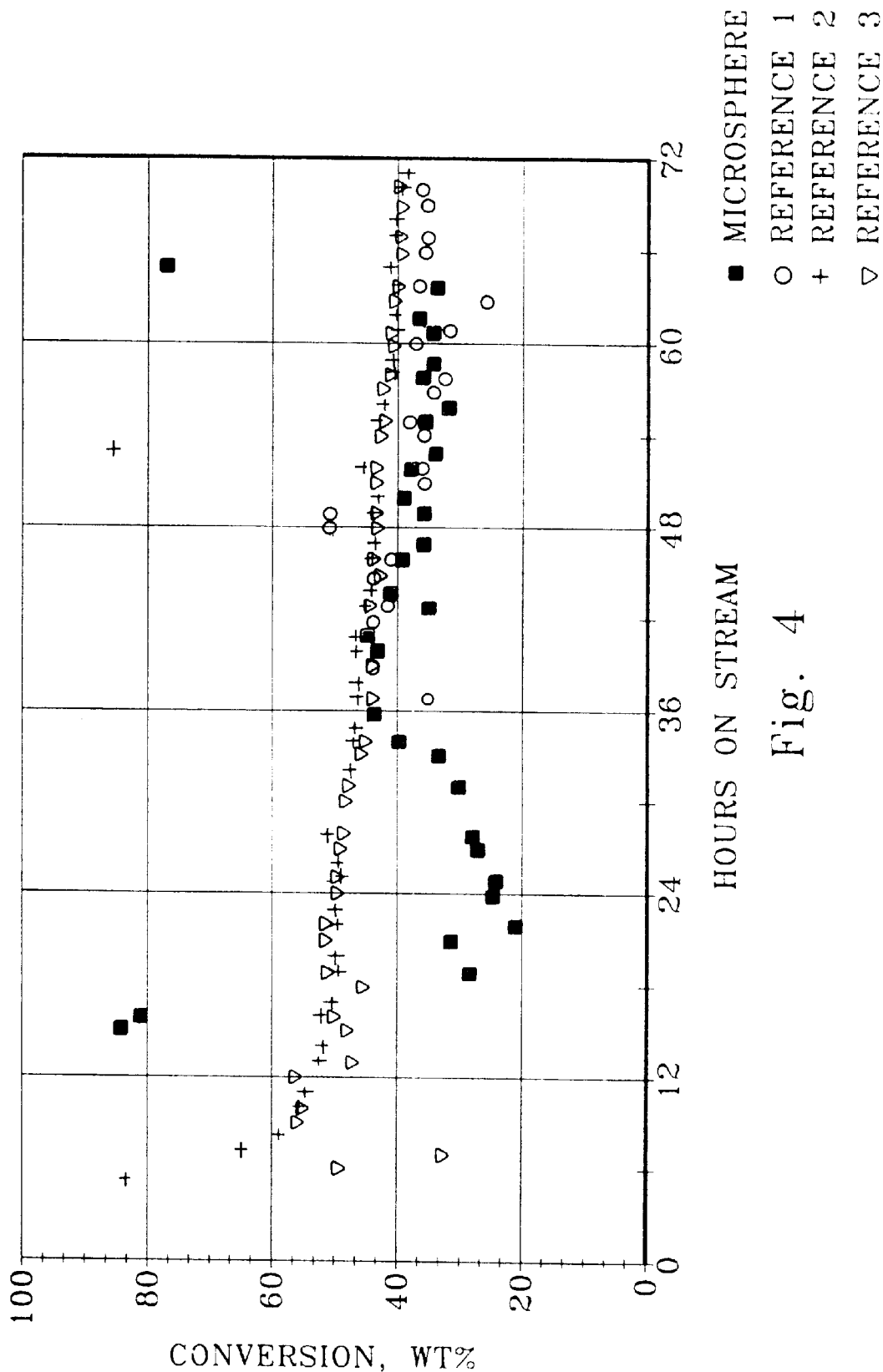
FIG. 4 shows weight percent hydrogen conversion over time when using a catalyst of the present invention as compared to three reference catalysts.
Figure 5:
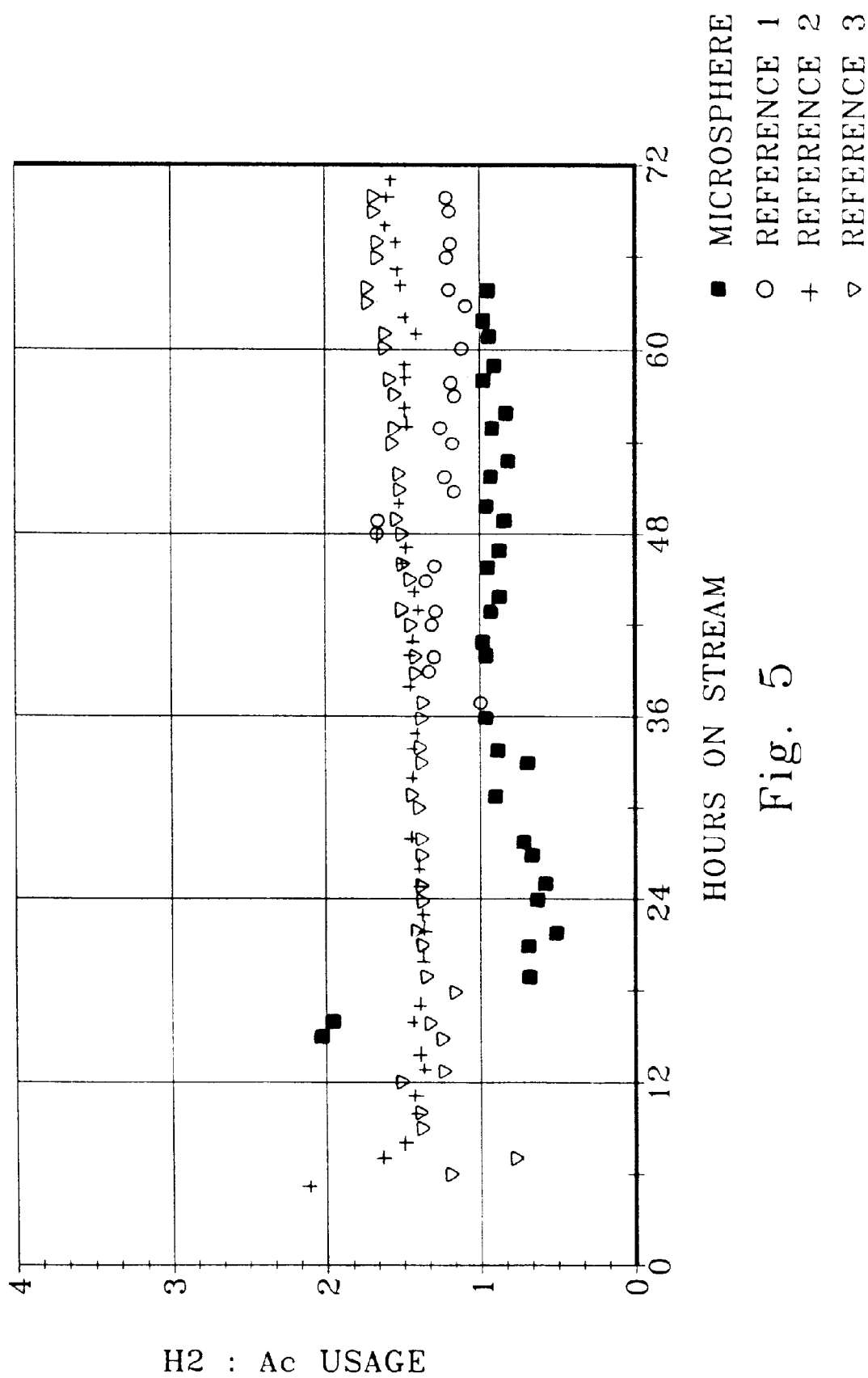
FIG. 5. shows the hydrogen:acetylene usage ratio (moles hydrogen consumed divided by moles acetylenes consumed) over time when using the catalyst of the present invention as compared to three reference catalysts.
Figure 6:
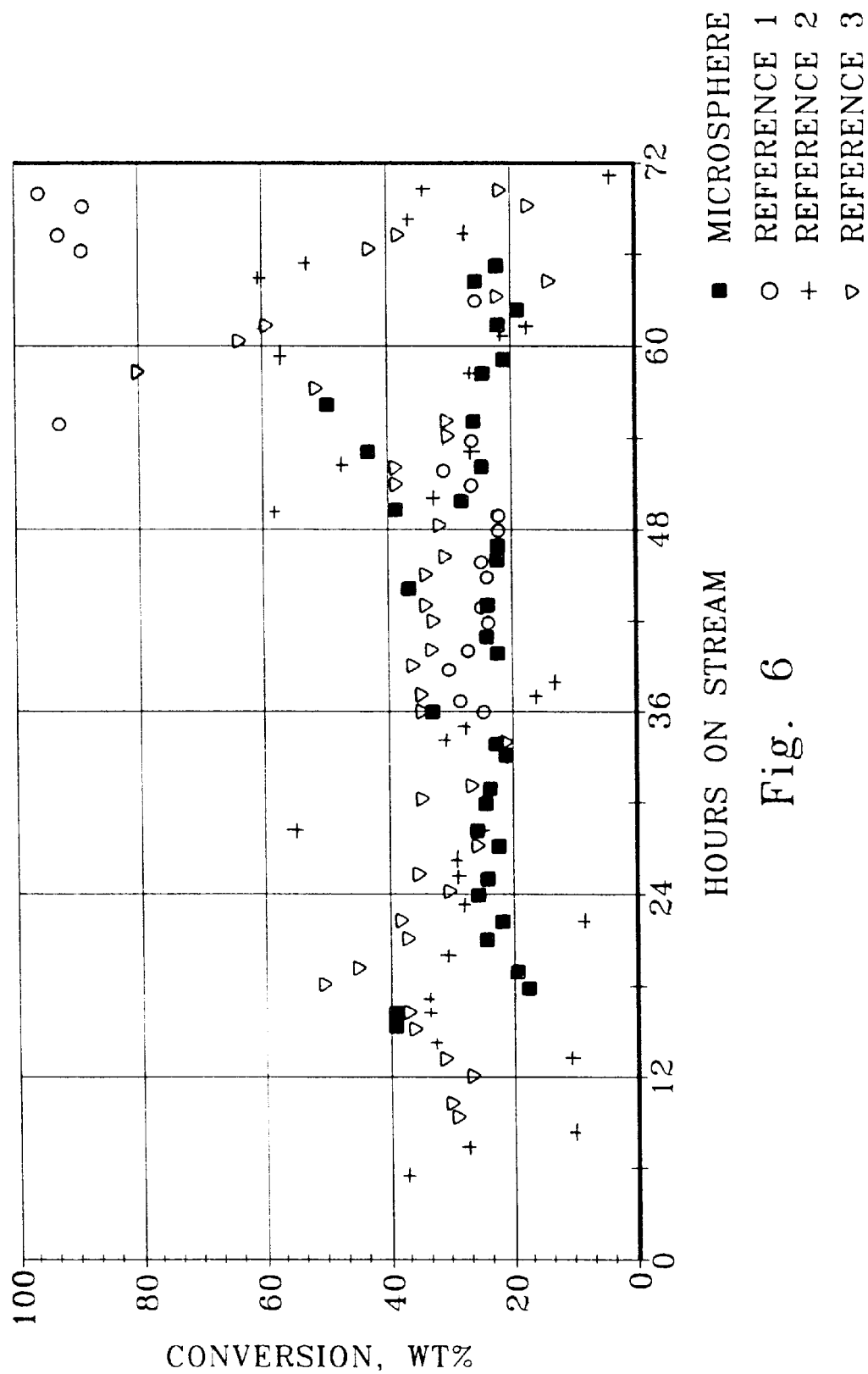
FIG. 6 shows selectivity to polymeric byproducts over time when using the catalyst of the present invention as compared to three reference catalysts.

FIG. 1 shows the weight percent conversion of vinyl acetylene that occurred over time during each of the experiments. The data clearly shows the increased stability of the microspherical catalyst over time as compared to the reference catalysts. The microspherical catalyst of Example 2 remained at greater than 90 weight percent conversion of vinyl acetylene for 70 hours on stream, while the reference catalysts of Example 1 showed less than 80 weight percent conversion at 70 hours on stream. Similarly, FIG. 2 shows the microspherical catalyst of Example 2 remained at greater than about 78 weight percent conversion of total acetylenes at 70 hours on stream, while the reference catalysts of Example 1 showed less than about 75 weight percent conversion total acetylenes at 70 hours on stream. The enhanced selectivity of the microspherical catalyst is demonstrated in FIG. 3 which shows higher butadiene retention (weight percent of butadiene in the effluent divided by weight percent butadiene in the feed) with the microspherical catalyst; in FIG. 4 which shows overall less hydrogen conversion when using the microspherical catalyst; and in FIG. 5 which shows lower hydrogen to acetylene usage ratio indicating that less hydrogen is being consumed through hydrogenation of butadiene when using the microspherical catalyst. FIG. 6 indicates that the selectivity for polymeric byproducts, or green oil, is less when using the microspherical catalyst of Example 1.

What is claimed is:

1. A process for selectively hydrogenating C4-acetylenes in a liquid hydrocarbon stream containing largely butadiene comprising contacting hydrogen and the hydrocarbon stream with a catalytic composite comprising an inorganic oxide support having dispersed thereon finely divided copper metal and an activator metal selected from the group consisting of nickel, cobalt, platinum, palladium, manganese, and a combination thereof said catalytic composite having an average effective diameter of about 1/32 inch (800 microns) wherein at least 70 weight percent of said copper metal and said activator metal are dispersed on the outer 200 microns layer of the support.

2. The process of claim 1 wherein the catalytic composite is of a shape selected from the group consisting of a sphere and an extrudate.

3. The process of claim 1 wherein at least 80 weight percent of said copper metal and said activator metal ed on the outer 200 micron layer of the support.

4. The process of claim 1 wherein the inorganic oxide support is selected from the group consisting of alumina, silica, magnesia, zirconia, and titania.

5. The process of claim 1 wherein the C4-acetylenes include ethylacetylene, methylacetylene and vinylacetylene.

6. The process of claim 1 wherein the selective hydrogenation conditions include a temperature of about 20° C. to about 80° C., a pressure of from about 15 bars to about 50 bars, a liquid hourly space velocity of from about 0.5 to about 10, and a hydrogen to acetylene ratio of about 1.0 to 5.0.

7. The process of claim 1 wherein said copper metal is present in an amount ranging from about 5 to about 15 weight percent of the catalytic composite.

8. The process of claim 1 wherein said activator metal is present in an amount ranging of from about 0.1 to about 1 weight percent of the catalytic composite.

* * * * *